(12) United States Patent
Yahagi et al.

(10) Patent No.: US 7,506,982 B2
(45) Date of Patent: Mar. 24, 2009

(54) OPHTHALMOLOGIC PHOTOGRAPHING APPARATUS

(75) Inventors: Ryoichi Yahagi, Itabashi-ku (JP);
Hiroyuki Ootsuka, Itabashi-ku (JP);
Takanori Takeda, Itabashi-ku (JP)

(73) Assignee: Kabushiki Kaisha TOPCON, Tokyo (JP)

( * ) Notice: Subject to any disclaimer, the term of this patent is extended or adjusted under 35 U.S.C. 154(b) by 0 days.

(21) Appl. No.: 11/980,042

(22) Filed: Oct. 30, 2007

(65) Prior Publication Data

US 2008/0100801 A1 May 1, 2008

(30) Foreign Application Priority Data

Oct. 31, 2006 (JP) ............................. 2006-296230

(51) Int. Cl.
*A61B 3/14* (2006.01)
*A61B 3/10* (2006.01)
(52) U.S. Cl. .................. 351/206; 351/210; 351/214
(58) Field of Classification Search ............... 351/205, 351/206, 210, 214
See application file for complete search history.

(56) References Cited

U.S. PATENT DOCUMENTS 7,241,011 B2 * 7/2007 Baek et al. ............... 351/206

FOREIGN PATENT DOCUMENTS

JP 2004-350849 12/2004

* cited by examiner

*Primary Examiner*—William C Choi
*Assistant Examiner*—Jack Dinh
(74) *Attorney, Agent, or Firm*—Chapman and Cutler LLP

(57) ABSTRACT

An opthalmologic photographing apparatus which is used to observe and photograph a fundus oculi of an eye to be examined, includes an observation light source illuminating the eye to observe the fundus oculi of the eye, a photographing light source illuminating the eye to photograph an image of the fundus oculi of the eye, an aperture through which light illuminated from either the observation light source or the photographing light source and reflected on the fundus oculi of the eye is observed or photographed, and a control device which is configured to control an opening area of the aperture. The control device sets the opening area of the aperture to an opened observing opening area when observing the fundus oculi, and to a narrowed photographing opening area when photographing the image of the fundus oculi.

10 Claims, 7 Drawing Sheets

OPHTHALMOLOGIC PHOTOGRAPHING APPARATUS

CROSS-REFERENCE TO THE RELATED APPLICATIONS

The present application is based on and claims priority from Japanese Application Number 2006-296230, filed on Oct. 31, 2006, the disclosure of which is hereby incorporated by reference herein in its entirety.

BACKGROUND OF THE INVENTION

1. Field of the Invention

The present invention relates to an opthalmologic photographing apparatus (also called a "fundus camera") used for examining the fundus oculi of an eye to be examined and photographing an image of the fundus oculi.

2. Description of the Related Art

In recent years, due to the increasing of the role of computers, the popularizing of video games and the increasing of the ageing population, the demand on opthalmological treatment and examination has been increased. Reflecting such a situation, the treatment and examination efficiencies based on developments of an opthalmologic apparatus in operability are becoming more important.

This trend also exists for opthalmologic photographing apparatus. Improvements has been made not only for hardware, but also for software, in order to achieve, for example, the coordination of various actions and the automation of various settings based on computer program controls.

Such as the software improvements aimed at enhancing efficiency and providing additional functions, the precision of the opthalmologic photographing apparatus as a counter balance must be maintained or even enhanced.

For example, selecting an appropriate aperture size is a key factor to increase the photographing precision. Determining a light volume of observation light and photographing light corresponding to the selected aperture also have a major effect on the photographing precision.

An opthalmologic photographing apparatus dealing with the above issues has therefore been proposed, which features increased operability, efficiency and photographing precision through the coordinated setting of an aperture used for photographing an image of a fundus oculi of an eye to be examined and an illumination light volume. As a selecting mode of the photographing aperture, a resolution priority mode and a depth priority mode may be selected. If the resolution priority mode is selected, an opening area of the aperture will be set from an initial value to a larger preset value, and if the depth priority mode is selected, the opening area will be set from an initial value to a smaller preset value and the light volume will be automatically adjusted in coordination with the altering of the aperture. (See Japanese Patent application Laid open No. 2004-350849)

The above opthalmologic photographing apparatus has been developed based on the following issues:

A CCD camera and a film camera have different resolution and sensitivity, which deems it necessary to change the opening area of the aperture in order to ensure a good precision (a setting of the resolution priority mode and the depth priority mode);

In a case where the opening area of the aperture has been changed, the photographing precise is decreased when the light volume is maintained without changes of the light volume, and the operation efficiency is adversely affected when the light volume is changed manually (an automatic adjustment of the light volume in coordination with changes of the aperture size).

In other words, the above opthalmologic apparatus has been proposed on the basis of the photographing of the image of the fundus oculi and particularly without considering appropriate the opening area of the aperture for related observation of the fundus oculi.

Accordingly, in the above opthalmologic photographing apparatus, the opening area of the aperture used to observe the fundus oculi will be set to a value (the initial value of the aperture), which is without using a priority mode, that is possible to set an intermediate aperture size between a larger and smaller values. However, when increasing the depth of field in observing the fundus oculi, narrowing the aperture is required, and the following problems may occur:

Focusing is difficult because of the dim observing image;

Larger depth of field for photographing the image of the fundus oculi leads to difficult focusing;

A narrowed aperture causes increased discomfort to the eye to be examined;

Even when dilated, pupils may still constrict when the luminous flux is high, leading to eclipses and flares.

The "depth of field" here refers to a range in which a subject is focused back and forth through the subject when being focused with a camera. A wider range means the depth of field is "larger", while a narrow range means a "smaller" depth of field.

SUMMARY OF THE INVENTION

The present invention has been made in view of the above-mentioned circumstances. It is related to an opthalmologic photographing apparatus that facilitates the observation of the fundus oculi while minimizes the discomfort on the eye to be examined, and also generates more clear photograph of the image of the fundus oculi of the eye.

To achieve the above object, an opthalmologic photographing apparatus according to an embodiment of the present invention which is used to observe and photograph a fundus oculi of an eye to be examined, include an observation light source illuminating the eye to observe the fundus oculi of the eye, a photographing light source illuminating the eye to photograph an image of the fundus oculi of the eye, an aperture through which light illuminated from either the observation light source or the photographing light source and reflected on the fundus oculi of the eye is observed or photographed, and a control device which is configured to control an opening area of the aperture. The control device sets the opening area of the aperture to an opened observing opening area to observe the fundus oculi, and to a narrowed photographing opening area to photograph the image of the fundus oculi.

DETAILED DESCRIPTION OF THE PREFERRED EMBODIMENTS

Preferred embodiments of the opthalmologic photographing apparatus according to the present invention will be described in accordance with the accompanying drawings.

Figure 3:
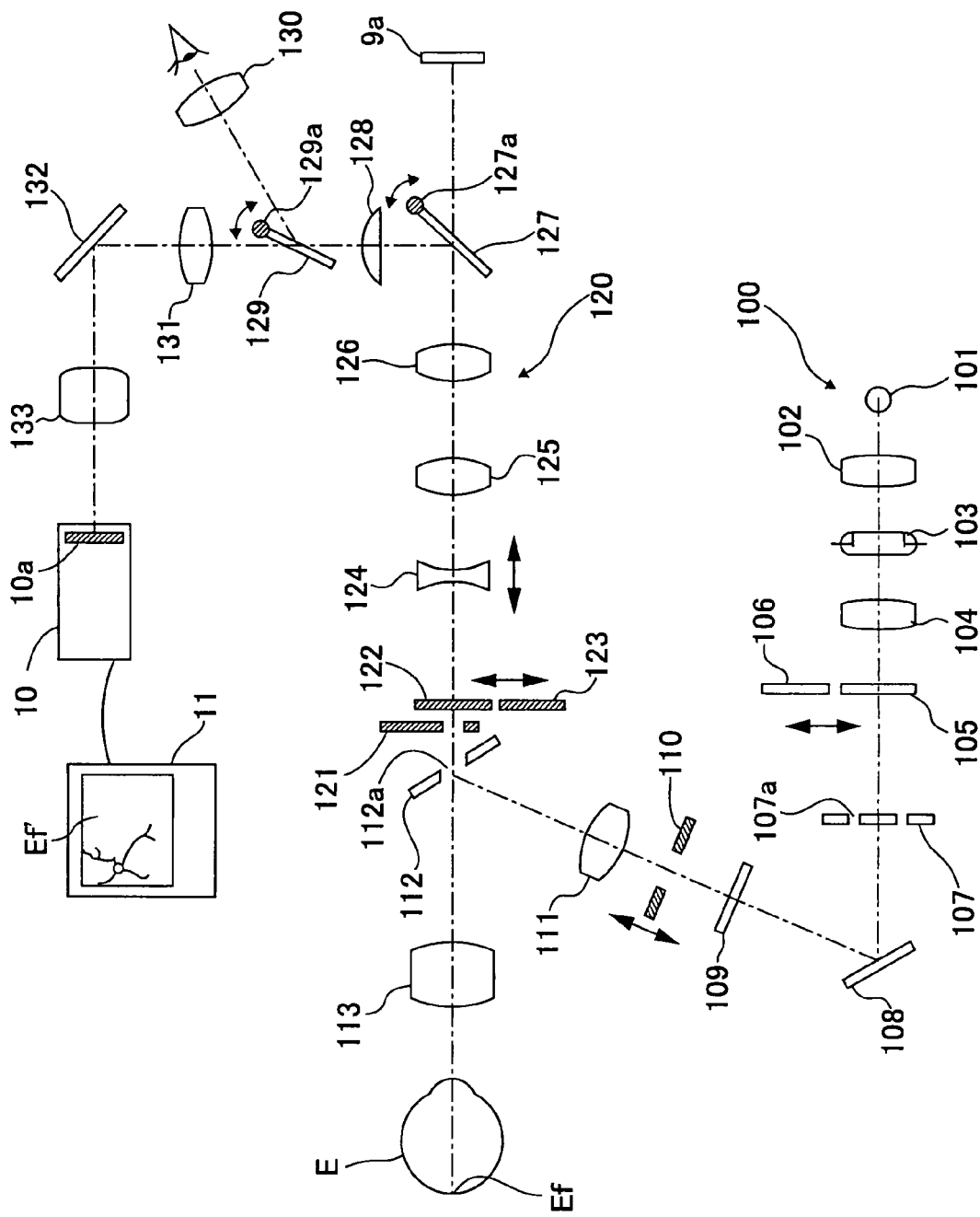
FIG. 3 is a schematic view illustrating an example of an optical system stored in a main body 8 of the opthalmologic photographing apparatus 1 according to the first embodiment of the present invention.

An opthalmologic photographing apparatus 1 according to an embodiment of the present invention is used, for example, to observe and photograph a fundus oculi Ef of an eye E to be examined. As shown in FIG. 3, the opthalmologic photographing apparatus 1 includes an observation light source 101 illuminating the eye E to observe the fundus oculi Ef of the eye E, a photographing light source 103 illuminating the eye E to photograph an image of the fundus oculi Ef of the eye E, an aperture 121 through which light illuminated from either the observation light source 101 or the photographing light source 103 and reflected on the fundus oculi Ef of the eye E is observed or photographed, and a control device (described below) which is configured to control an opening area of the aperture. The control device sets the opening area of the aperture 121 to an opened observing opening area to observe the fundus oculi Ef, and to a narrowed photographing opening area to photograph the image of the fundus oculi Ef.

First Embodiment

Structures of an opthalmologic photographing apparatus according to a first embodiment of the present invention is described herein.

[Outer Structure]

Figure 1:
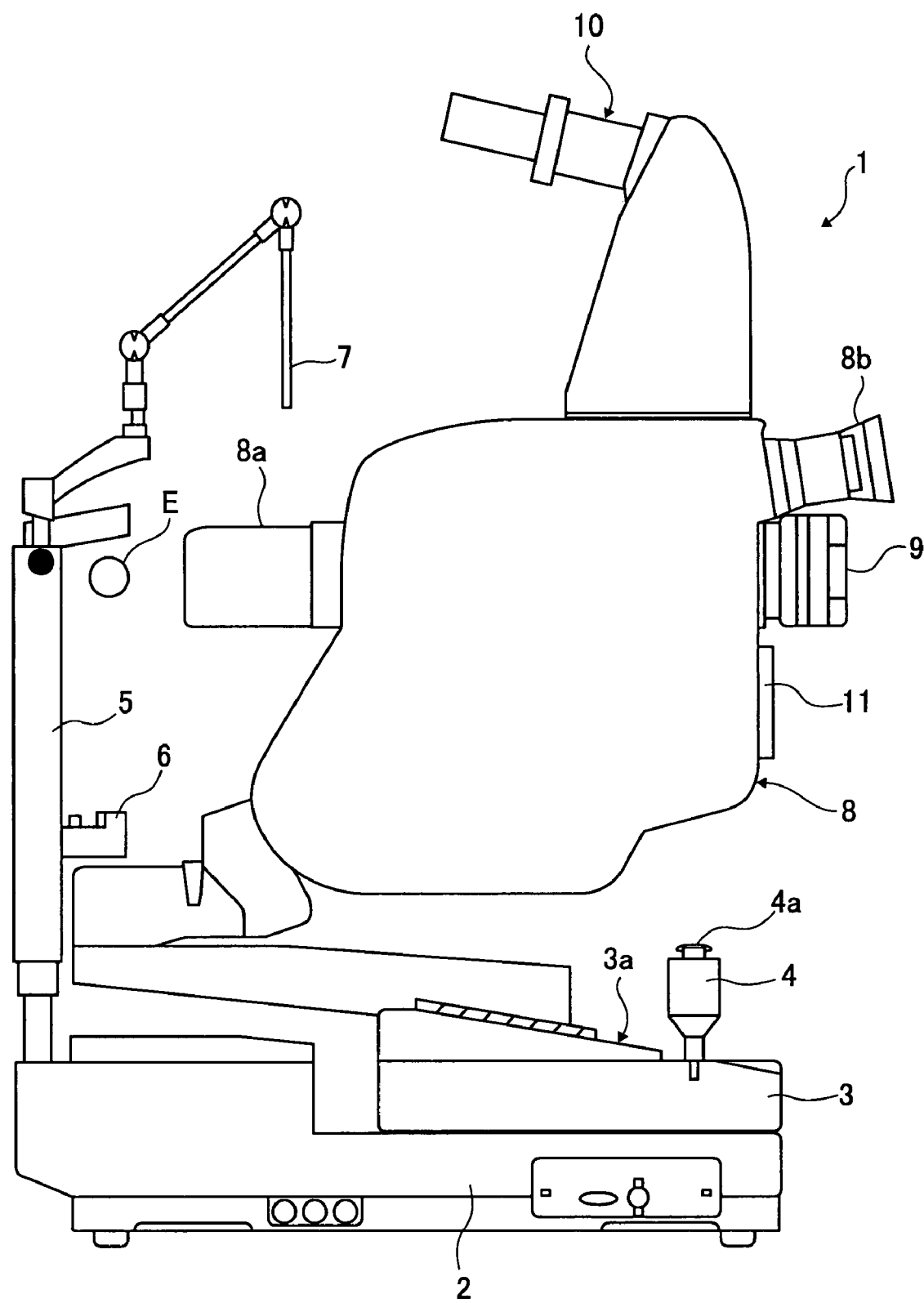
FIG. 1 is a side view illustrating an outer structure of an opthalmologic photographing apparatus 1 according to a first embodiment of the present invention.
Figure 2A:
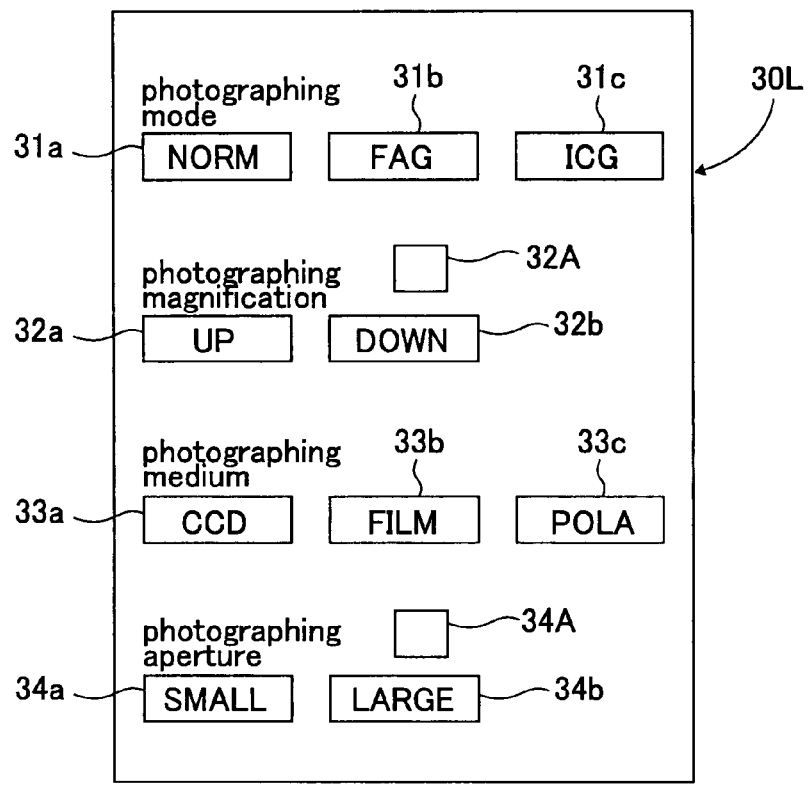
FIG. 2A is a view illustrating an example of a first and a second control panel of the opthalmologic photographing apparatus 1 according to the first embodiment of the present invention.

FIG. 1 is a side view illustrating an opthalmologic photographing apparatus 1 according to a first embodiment. FIG. 2 is a view illustrating an example of a first and a second control panels in the opthalmologic photographing apparatus 1 of the first embodiment. The outer structure of the apparatus will be described in accordance with these drawings.

As illustrated in FIG. 1, the opthalmologic photographing apparatus 1 of the first embodiment includes a base 2 and a mount 3 provided on the base 2 slidably from front to back and from side to side in a horizontal direction.

The mount 3 is provided with a control lever 4, through which the examiner can move freely the mount 3 on the base 2. In addition, an upper part of the control lever 4 is provided with a photographing button 4a, which allows an image of a fundus oculi to be photographed by a button operation.

Provided on the base 2 is a supporter 5 on which a chin receiver 6 for placing a chin of a person which has an eye to be examined and an external fixation lamp 7 which is a light source for fixating the eye to be examined E are provided.

A main body 8 which houses each kind of optical systems and control systems of the opthalmologic photographing apparatus 1 is provided on the mount 3. In addition, it is possible that the control systems is provided inside the base 2 or the mount 3.

The main body 8 is provided with an objective lens part 8a opposite to the eye E, and an eyepiece lens part 8b used for observing the eye E.

The main body 8 is connected to a first imaging device 9 which is configured to photograph a still image of the fundus oculi of the eye E, and a second imaging device 10 which is configured to photograph an image of a fundus oculi of the eye E, such as a television camera. The first imaging device 9 and the second imaging device 10 are removably connected to the main body 8. Particularly, as the first imaging device 9, it is possible that a camera such as a CCD camera, a film camera (for example 35 mm) or an instant camera is connected accordingly, in accordance with the purpose of the observation. Also, if at least one of the first imaging device 9 and the second imaging device 10 is a digital imaging device, it is possible to send and store the image obtained by the first imaging device 9 or the second imaging device 10 to an image recorder (the details will be described later), which is formed from such as a computer provided on an external of the opthalmologic photographing apparatus.

A color liquid crystal monitor 11 is provided at an examiner side of the main body 8. The liquid crystal monitor 11 displays the image of the fundus oculi of the eye E based on an image signal obtained by the second photographing device 10.

As illustrated in FIG. 2, a control panel 30 is provided on an upper surface 3a of the mount 3. The control panel 30 includes a plurality of buttons and a display unit which allows various settings and confirmation of statuses of photographing. It is possible to set such as the photographing mode, a magnification, a type of medium which forms the first imaging device 9, an opening area of the aperture, and a photographing field angle, to confirm such as an aperture value of the aperture, and to shift a fixation target. The details will be described later.

Figure 2B:
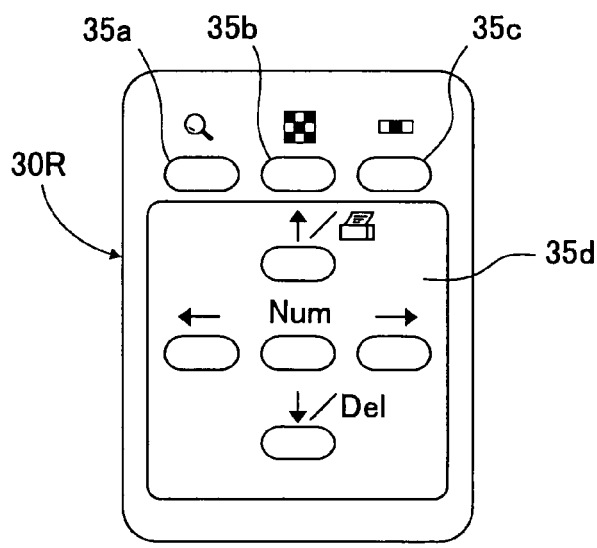
FIG. 2B is a view illustrating an example of a first and a second control panel of the opthalmologic photographing apparatus 1 according to the first embodiment of the present invention.

The control panel 30 is provided with a first control panel 30L provided on an upper part of a left side of the upper surface 3a of the mount 3 (FIG. 2A), and a second control panel 30R provided on an upper part of a right side of the upper surface 3a of the mount 3 (FIG. 2B).

The first control panel 30L is also provided with a NORM button 31a for selecting a normal color photographing mode, a FAG button 31b for selecting a visible fluorescence photographing mode (FAG photographing mode), and an ICG button 31c for selecting an infrared fluorescence photographing mode (ICG photographing mode), as buttons for setting the photographing mode. The color photographing mode is selected to be an initial setting of the photographing mode.

The first control panel 30L is also provided with an UP button 32a for increasing the photographing magnification and a DOWN button 32b for decreasing it, as buttons for setting the photographing magnification. A display 32A is also provided for displaying a set photographing magnification.

The first control panel 30L is also provided with a CCD button 33a to be selected when a CCD camera is connected, a FILM button 33b to be selected when a film camera is connected, and a POLA button 33c to be selected when an instant camera is connected, as buttons for setting the type of photographing medium (photographing medium setting device) used. The CCD camera is selected as an initial setting of the photographing medium.

The first control panel 30L is also provided with a SMALL button 34a for setting an opening area of the aperture 121 to a target photographing opening area which is used when photographing with a depth of field being deep, and a LARGE button 34b for setting the opening area of the aperture 121 to a target observing opening area which is used when observing with the depth of field being shallow, as buttons for setting the opening area of the aperture 121. A display 34A (aperture setting device) is also provided for displaying information about the aperture value of the aperture 121. LARGE (opening aperture) is selected to be the initial setting of the aperture.

The second control panel 30R is provided with a field angle switch 35a for switching an incident angle to a pupil when observing or photographing the image of the fundus oculi, a thumbnail switch 35b for displaying a list of a plurality of the images of the fundus oculi, a fixation shift switch 35c for shifting a location of an internal fixation target (LCD display 109), and a number switch 35d used for setting various numbers.

It is possible that the control panel 30 to be provided with other various buttons, switches and displays or the like. For example, a button for setting and manipulating a timer, a display for displaying the timer, a button for manually adjusting an illumination light volume for observing and photographing, a display for displaying the illumination light volume, a display for displaying the photographing field angle, switches for switching ON/OF of various illumination light, and a display indicating that whether the eye E is a left eye or a right eye or the like are possible to be provided.

[Structure of the Optical System]

Figure 4:
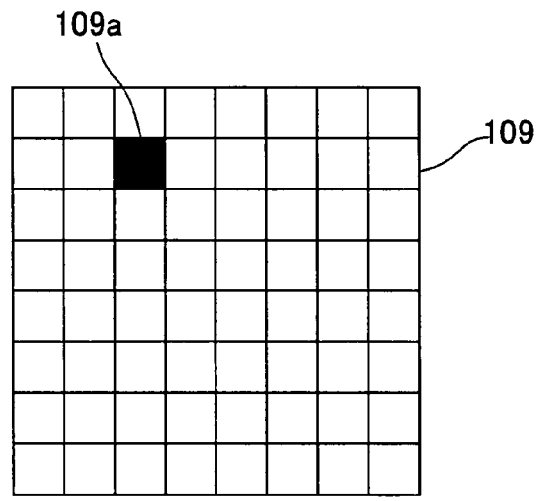
FIG. 4 is a view illustrating an example of a fixation target 109a, which is formed from dots by an LCD 109 provided in an illumination optical system 100 in an optical system.
Figure 5:
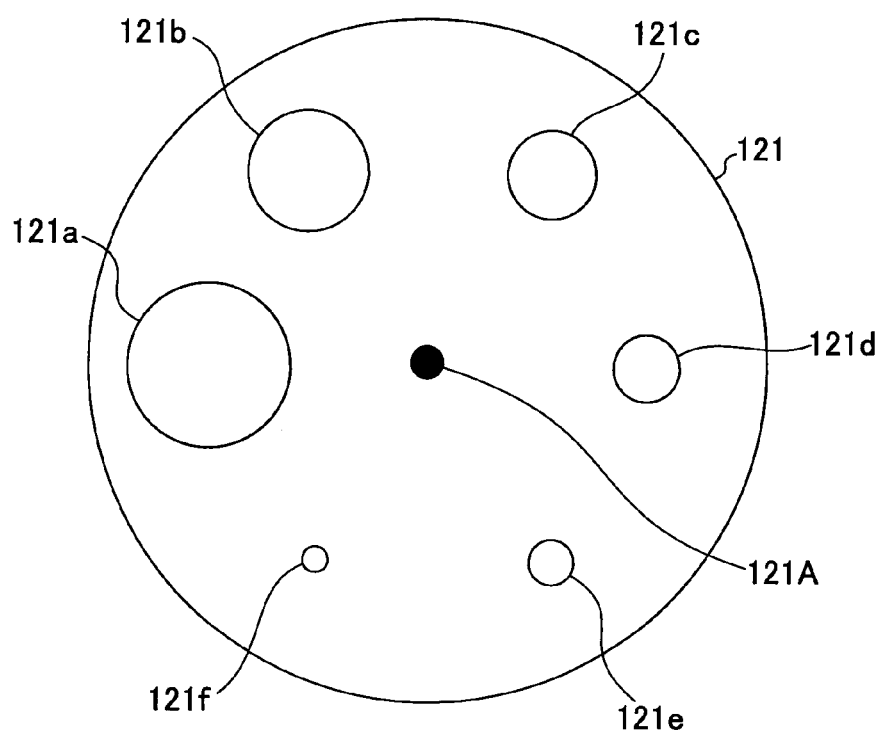
FIG. 5 is a schematic view illustrating an example of an aperture 121 provided in a photographing optical system 120 in the optical system.

FIG. 3 is a schematic view illustrating an example of an optical system stored in the main body 8 of the opthalmologic photographing apparatus according to the first embodiment of the present invention. FIG. 4 illustrates an example of a fixation target 109a, which is formed from dots by an LCD 109 provided in the illumination optical system 100 within an optical system. FIG. 5 is a schematic view illustrating an example of the aperture 121 provided in a photographing optical system 120 within the optical system.

The opthalmologic photographing apparatus 1 of the first embodiment includes an illumination optical system 100 for illuminating the fundus oculi Ef of the eye E, and a photographing optical system 120 for observing and photographing the illuminated fundus oculi Ef.

As illustrated in FIG. 3, the optical system 100 has a halogen lamp 101 as the observation light source, a condensing lens 102, a xenon lamp 103 as the photographing light source, a condensing lens 104, an exciter filter 105 and an exciter filter 106, a ring aperture plate 107 with a ring-shaped opening, a mirror 108, a LCD display 109, an illumination aperture 110, a relay lens 111, a holed mirror 112, and an objective lens 113, which are arranged in this sequence.

The halogen lamp 101 is a continuously emitting light-source which is lighting when an examiner observes the eye E or conducts color photography of the image of the fundus oculi. It serves as a photographing light source and an observation light source of the present invention.

The condensing lens 102 is an optical element, which focuses observation light from the halogen lamp 101, and illuminates the eye E (especially its fundus oculi Ef) uniformly.

The xenon lamp 103 is a light source which is lighting when a fluorescence photographing of the fundus oculi Ef is conducted.

The condensing lens 104 is an optical element for focusing the observation light from the xenon lamp 103 and illuminates the fundus oculi Ef uniformly.

The exciter filters 105 and 106 are used when a fluorescence photographing of the image of the fundus oculi Ef is conducted. They are removably provided on a light path by means of a solenoid, which will be described later. Under the FAG photographing mode, only the exciter filter 105 is inserted in the light path. Under the ICG photographing mode, only the exciter filter 106 is inserted in the light path. Under the normal color photographing mode, both of the exciter filters are removed from the light path.

The ring aperture plate 107 has a ring aperture 107a which is centered on an optical axis and is disposed to be conjugate to the pupil of the eye E.

The mirror 108 is an optical element which reflects light from the halogen lamp 101 or the xenon lamp 103 and slants the light towards the optical axis of the photographing optical system 120.

As illustrated in FIG. 4, the LCD 109 is a device that forms a fixation target 109a which is formed from dots to allow the eye E to be fixed on, to change the position of the dot displaying, and to direct a sight-direction of the eye E. However, the LCD 109 is also centered on a point conjugate to the fundus Ef, so the fixation target 109a is configured to be imaged on the fundus oculi Ef.

The illumination aperture 110 is an aperture for shielding from lights out of the illumination area in order to eliminate flare, and it is configured to be capable of changing the illumination area, and disposed movably along the axis direction by a solenoid described below.

The holed mirror 112 is a combine member which combines an axis of the illumination optical system 100 and an axis of the photographing optical system 120, and a hole 112a is formed approximately on the intersection of the two axes. The objective lens 113 is provided in the objective lens part 8a of the main body 8.

In addition, as illustrated in FIG. 3, the photographing optical system 120 which is used for observing the fundus oculi Ef of the eye Ef and for conducting photographing of the fundus oculi Ef, includes an objective lens 113, the hole 112a on the holed mirror 112, an aperture 121, shielding filters 122 and 123, a focusing lens 124, a fixed lens 125, a photographing lens 126, and a quick return mirror 127, in this sequence.

In addition, reference number 9a in FIG. 3 indicates a photographing medium of the first photographing device 9, i.e., a CCD, a 35 mm camera film (hereinafter, refers film) or an instant camera film or the like.

The aperture 121 is ring-shaped, as illustrated in FIG. 5. It is centered on a shaft 121A driven by a solenoid described later. The aperture 121 is also provided with plurality of holes (i.e., six) of different sizes serving as an aperture. The illustrated aperture contains six holes, from large to small, 121a, 121b, 121c, 121d, 121e, and 121f. When a size of the hole (opening area) becomes larger, an aperture value becomes smaller, and vice versa. The shielding filters 122 and 123 are removably disposed in the light path by means of a solenoid, which will be discussed later. Under the FAG photographing mode, only the shielding filter 122 is inserted in the light path. Under the ICG photographing mode, only the exciter filter 123 is inserted in the light path. Under the color photographing mode, both of the exciter filters are removed from the light path.

The focusing lens 124 is a lens which is capable of being moved along the axis direction to focus the image of the fundus oculi Ef. The photographing lens 126 is an optical element for imaging light beam from the eye E onto the photographing medium 9a.

The quick return mirror 127 is configured to be capable of rotating around a shaft 127a, and is flipped-up when photographing the image of the fundus oculi Ef by the first photographing device 9, and it is configured to lead the light from the eye E to the photographing medium 9a. When observing the eye E or photographing the fundus oculi by the second photographing device 10, the quick return mirror 127 is configured to be inclined on the light path and to deflect and slant the light beam.

As illustrated in FIG. 3, the photographing optical system 120 is further provided with a FOV lens (field lens) 128 for directing the light deflected by the quick return mirror 127, a switching mirror 129, an eyepiece lens 130, a relay lens 131, a mirror 132, and a relay lens 133.

The switching mirror 129 is configured to be capable of rotating around a rotating shaft 129a. When observing the eye E, the mirror 129 is configured to be inclined in the light path, and to deflect the light beam towards the eyepiece lens 130. When using the second photographing device 10 for photographing the fundus oculi Ef, the mirror 129 is configured to be evacuated from the light path. In this time, the light beam is projected on a photographing element 10a through the relay lens 131, the mirror 132 and the relay lens 133. The image Ef' of the fundus oculi Ef photographed by the second photographing device 10 is configured to be displayed on the color LCD 11.

[Configurations of the Control System]

Figure 6:
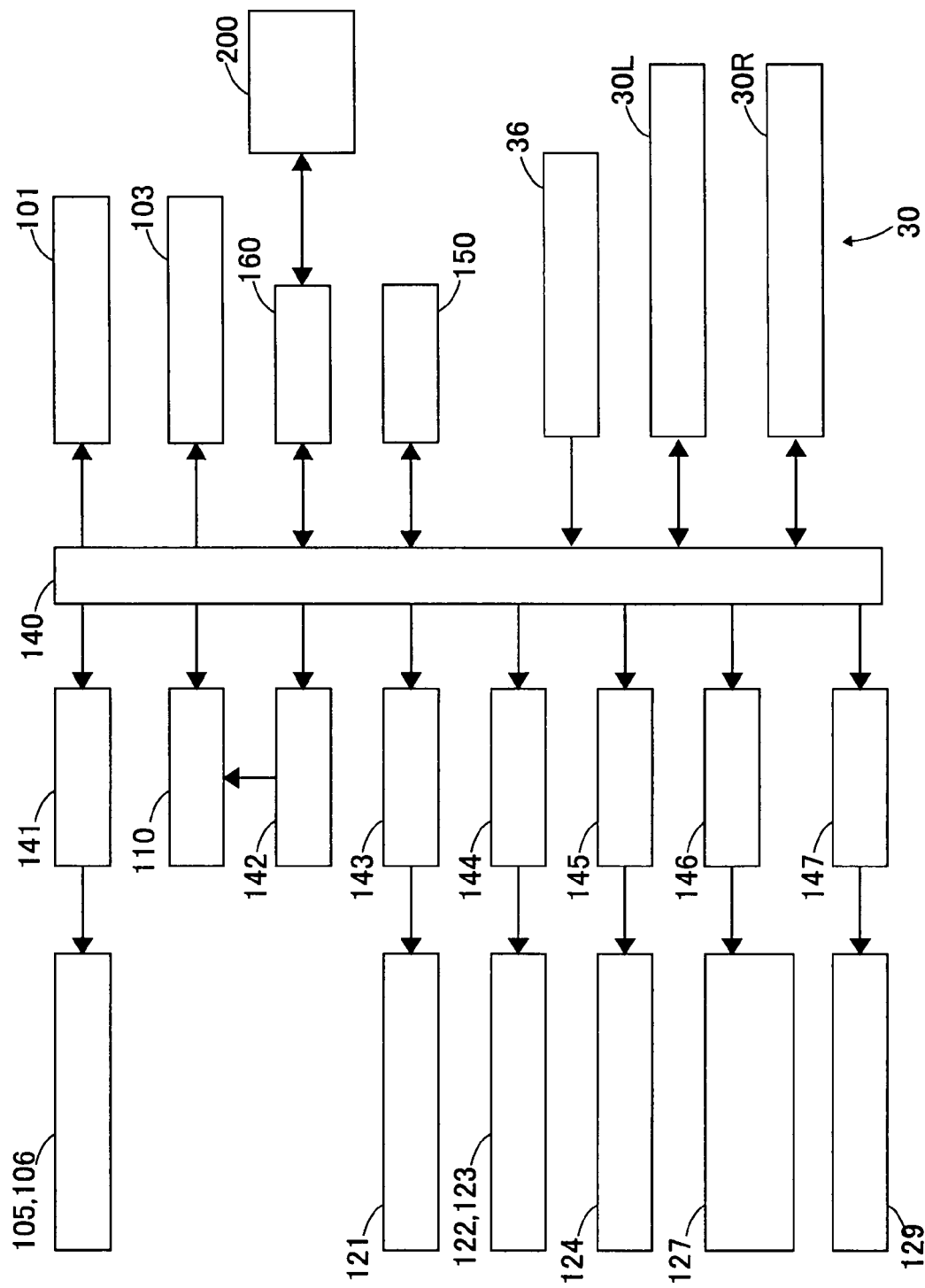
FIG. 6 is a control block diagram illustrating an example of a control system to control each part in the opthalmologic photographing apparatus according to the first embodiment of the present invention.

FIG. 6 is a block diagram illustrating an example of a control system for the opthalmologic photographing apparatus 1 of the first embodiment of the present invention. The control system will now be described in accordance with FIG. 6.

As illustrated in FIG. 6, the control system of the opthalmologic photographing apparatus 1 is mainly provided with a control device 140 and a storage device 150. The control device 140 includes an arithmetic-control unit, such as a CPU for carrying out various arithmetics and controls, and a storage unit such as a RAM for storing relevant computer programs and data. The storage device 150 stores the computer programs, such as the control program of the opthalmologic photographing apparatus 1, and the like and relevant data. The control device 140 is configured to control the opthalmologic photographing apparatus 1 based on the programs and image data stored in the storage device 150.

The opthalmologic photographing apparatus 1 is connected to an image recorder 200 for recording the photographed images. The control device 140 carries out, for example, transmission of the image data, via an interface unit (I/F) 160 as an interface for transmitting and receiving data with the image recorder 200.

As an alternative to the image recorder 200 provided outside of the opthalmologic photographing apparatus 1, it is possible that an internal image recorder is provided in the opthalmologic photographing apparatus 1, such as buffer storage.

Also, as the image recorder 200 when using an information processing device such as a computer, 200, a monitor of the image recorder 200 is configured to be capable of displaying setting and operation screens similar to the control panel 30, using the setting screen. It is possible that the setting and operation are carried out.

As illustrated in FIG. 6, the control device 140 is connected with the halogen lamp 101, the xenon lamp 103, the first control panel 30L, the second control panel 30R, a fixation position sensor 36 (fixation target position sensor as a fixation target position detection device) for detecting the position of the fixation target 109a, the illumination aperture 110, and solenoids 141, 142, 143, 144, 145, 146 and 147.

The fixation position sensor 36 is a sensor to detect at least one of positions, that is to say, one position is the position of the LCD 109 which is an internal fixation target and directs the fixation position of the eye, and the other position is the position of the external fixation lamp 7 which is an external fixation target and directs the fixation position of the eye E.

The solenoid 141 is used to move the exciter filters 105 and 106 in and out of the light path. The solenoid 142 is used to move the illumination aperture 110 along the optical axis direction. The solenoid 143 rotates the aperture 121 around the rotation shaft 121A. The solenoid 144 is used to move the shielding filters 122 and 123 in and out of the light path. The solenoid 145 moves the focusing lens 124 along the axis for focusing. The solenoid 146 rotates the quick return mirror 127 around the rotation shaft 127a. The solenoid 147 rotates the switching mirror 129 around the rotating shaft 129a. The control device 140 controls the on/off status and brightness of the halogen lamp 101 and the xenon lamp 103. The control device 140 is also configured to change the size of the aperture 121 and the illumination aperture 110.

The control device 140 receives various input/setting from the first control panel 30L, the second control panel 30R and the fixation position sensor 36, and manipulates the relevant parts. It should be noted that the buttons on the control panels 30L and 30R are omitted from FIG. 6 for simplicity.

The control device 140 is configured to display information for displaying the aperture size of the aperture 121 on the display part 34A of the first control panel 30L.

The information on the aperture size is as follows. As illustrated in FIG. 5, the aperture 121 is provided with holes 121a to 121f of different sizes to be used as various apertures values. When the aperture 121a is placed on the optical axis, the display part 34A shows "1"; when aperture 121b is placed on the optical axis, the display part 34A shows "2"; when aperture 121c is placed on the optical axis, the display part 34A shows "3"; when aperture 121d is placed on the optical axis, the display part 34A shows "4"; when aperture 121e is placed on the optical axis, the display part 34A shows "5"; and when aperture 121f is placed on the optical axis, the display part 34A shows "6". In other words, the size of the aperture 121 are configured to be displayed from the smallest to the largest aperture size, number "1" to "6".

As an alternative to display numbers corresponding to apertures 121a to 121f provided on such as the light path, it is possible that the aperture opening area of the aperture is displayed. In the other words, the displaying status by the display part 34A is any of status, if it indicates the size of the aperture 121.

The operations of the first embodiment will now be described.

Figure 7:
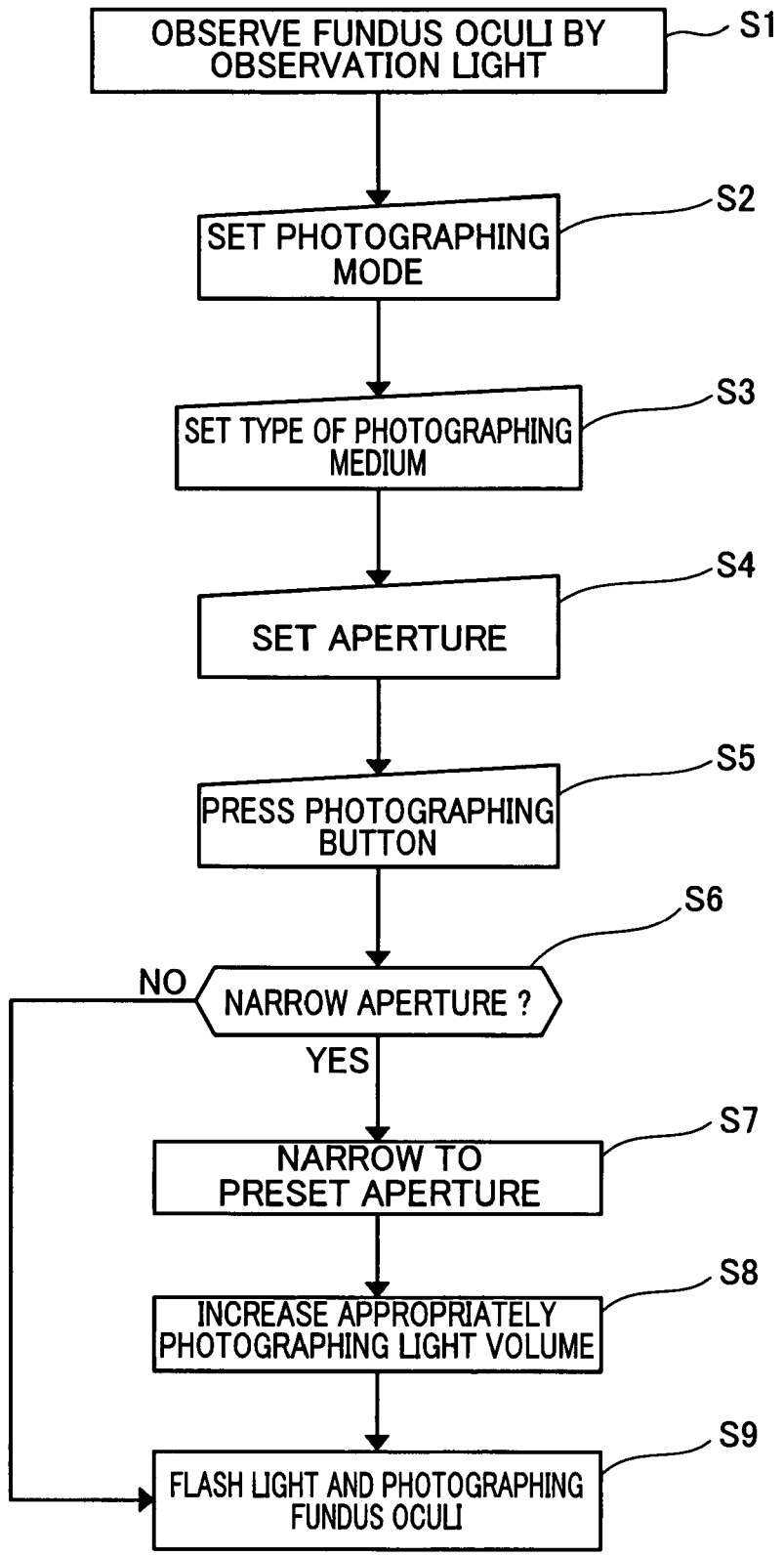
FIG. 7 is a flow chart illustrating an example of a process to observe and photograph a fundus oculi, which is carried out by use of the opthalmologic photographing apparatus according to the first embodiment of the present invention.

FIG. 7 is a flow chart illustrating an example of the processes for observing and photographing the image of the fundus oculi carried out by use of the opthalmologic photographing apparatus 1 of the first embodiment of the present invention. The operations of observing the fundus oculi, photographing the image of the fundus oculi, and switching the aperture between when observing and photographing in accordance with FIG. 7.

[Fundus Image Observation]

In step S1, the aperture 121 is set to an opening state, and the light volume of the halogen lamp 101 is automatically reduced in coordination with the opening state of the aperture 121. The image of the fundus oculi of the eye E is observed by use of the observation light having a reduced light volume.

To observe the fundus oculi of the eye E, the examined person is firstly asked to sit on a chair (not illustrated) and to put his/her chin on the chin receiver 6. The optical system is then aligned in relation to the eye E. The alignment of the optical system in relation to the eye E is carried out by moving the mount 3 in horizontal and anteroposterior directions on the base 2 through the control lever 4, until the eye E is displayed at the center of the color LCD 11 (anterior segment observation).

Then, when the mount 3 is moved by the control lever 4 so that a displayed position of the eye E is changed from the anterior segment of the eye E as the anterior segment observation to the fundus oculi Ef in a state in which a defocus image of the fundus oculi Ef is displayed, via the pupil. In this state, for example, by manipulating the control lever 4 so as to match two alignment points into one, and to put the matched alignment point into inside of "( ) scale" on the color LCD 11, focusing the fundus oculi Ef is carried out, and the fundus oculi Ef of the eye E is displayed on the color LED 11 (the fundus oculi observation).

When observing the fundus oculi Ef, the aperture 121 as an initial state which is an opened state (for example, by placing a larger aperture 121a, 121b or 121c with the opening area on the axis of the photographing optical system 120). The light volume of the halogen lamp 101 is automatically reduced in coordination with the opening state of the aperture 121.

The observation light emitted from the halogen lamp 110 illuminates the ring opened plate 107 via the condensing lenses 102 and 104. After going through the ring-shaped opening 107a of the plate 107, the light is deflected by mirror 108, is passed via the LCD 109, the illumination aperture 110 and the relay lens 111, is deflected again by the holed mirror 112 in the direction of the optical axis of the photographing optical system 120 and is finally illuminating the eye E through the objective lens 113. Herein, because of the conjugate positioning of the ring-shaped plate 107 to the pupil of the eye E, a ring-shaped image is formed on the pupil, by which the fundus oculi Ef is illuminated.

[Fundus Oculi Image Photographing Operations]

In step S2, after the fundus oculi observation, one of the buttons 31a, 31b and 31c disposed on the first control panel 30L is selectively pressed to set to the photographing mode. When the photographing mode setting is defaulted, the color photographing mode corresponding to the button 31a is selected as the initial setting.

The pressed button is configured to be lighted to confirm which mode has been selected. The selected photographing mode is stored in the storage device 150 or the RAM of the control device 140 as setting information. The control device 140 controls the various part setting corresponding to the selected photographing mode. For example, when the color photographing mode corresponding to the button 31a is selected, the halogen lamp 101 is controlled to light up; on the other hand, when the FAG mode or the ICG mode corresponding to the button 31b or 31c, respectively, is selected, the xenon lamp 103 will be controlled to light up.

In step S3, one of the buttons 33a, 33b and 33c is selectively pressed to set the type of photographing medium used by the first imaging device 9. If the type of the medium is not set, the CCD camera corresponding to the button 33a is selected as the initial setting. The pressed button is configured to be lighted to confirm which type of photographing medium has been selected. The selected medium type is stored in the storage device 150 or the RAM of the control device 140 as setting condition information. In step S4, the button 34a or 34b is pressed to set the opening area of the aperture 121. When the opening area of the aperture 121 is not set, the "LARGE" (opened aperture) corresponding to the button 34b is selected as initial setting.

In this time, the set opening area of the aperture 121 is stored in the storage device 150 or the RAM of the control device 140 as setting condition information.

In step S5, after some or all or none of the above setting operations, the button 4a is pressed as the fundus oculi photographing operation. In other words, it is possible that the setting operations in steps S2 to S4 are conducted in any order, or partially, or not at all. This does not affect the carrying out of the photographing operation in any way.

In step S6, following the process in step S5, in which the button 4a is pressed, it is determined whether the aperture 121 is required to be narrowed. If yes, the process proceeds to step S7; otherwise, the process proceeds to step S9.

It is determined that the aperture 121 is narrowed regardless of the photographing mode selected in step S2 (e.g., color photographing mode selection), or the medium type selected in step S3 (e.g., CCD camera selection). In a case that SMALL button 34a, which corresponds to the "SMALL" aperture size setting, is pressed in step S4, it is determined that the aperture 121 is narrowed based on only the selection of the aperture as a required condition to proceed to step S7.

In step S7, following determining that the aperture 121 is required to be narrowed in step S6, a control command is sent to the solenoid 143 to reduce the opening area of the aperture 121 from the "LARGE" (opening aperture) setting to the "SMALL" (small opening area aperture) setting.

The opening area of the aperture under the "LARGE" setting may be four times of that under the "SMALL" setting, for example, S LARGE:S SMALL=4:1.

In step S8, after the aperture 121 is controlled to be narrowed in step S7, the photographing light volume of the halogen lamp 101 and the xenon lamp 103 is appropriately increased in coordination with the change of the opening area of the aperture 121.

Herein, it is possible that the control amount to appropriately increase the photographing light volume is obtained through calculations based on information about the change of the aperture opening area. In addition, it is also possible that a table in which the information about the change of the aperture size is associated with the light volume is preliminarily stored in the storage device 150 or the like, to calculate the photographing light volume with reference to the table.

In step S9, after determining that the photographing light volume is increased in step S8, or that the aperture 121 is not required to be narrowed in step S6, flash is emitted from the xenon lamp 103 to conduct fluorescence photographing of the image Ef of the fundus oculi Ef of the eye E.

The control device 140 sends and stores the photographed image of the fundus oculi Ef to the image recorder 200, along with the opening area of the aperture 121 and the photographing light volume via the interface 160 (I/F unit).

When conducting the fluorescence photographing, the xenon lamp 103 illuminates the fundus oculi as well as the halogen lamp 101. At this time, one of the exciter filters 105 and 106 is selectively inserted on the light path in accordance with the visible fluorescence photographing or infrared fluorescence photographing.

[Aperture Switching Control in Observation and Photographing]

When the process is shifted from the observation operation to the photographing operation, in step S4, if the SMALL button 34a is not pressed, the aperture condition is not established, the process in the flow chart of FIG. 7 proceeds to step S1, step S2, step S3, step S4, step S5. step S6, and step S9 in this order.

Therefore, in step S9, the fluorescence photography of the image Ef of the fundus oculi Ef of the eye E is conducted with the aperture 121 set to "LARGE" (opening aperture).

On the other hand, when the process is shifted from the observation operation to the photographing operation, if the SMALL button 34a is pressed in step S4, the aperture condition is established, the process in the flow chart of FIG. 7 proceeds to step S1, step S2, step S3, step S4, step S5, step S6, step S7, step S8, and step S9, in this order.

Therefore, in step S7, when the aperture 121 is changed to be narrowed from the "LARGE" setting to "SMALL"; and in step S8, the aperture 121 is set to a condition in which an appropriate photographing light volume when the aperture is set to SMALL, is obtained. In step S9, the fluorescence photographing of the image Ef of the fundus oculi Ef of the eye E is conducted.

Therefore, in the opthalmologic photographing apparatus 1 of the first embodiment, the opening area of the aperture 121 is set to "LARGE" when observing the fundus oculi, and is set to be narrowed to "SMALL" when conducting the fundus image photography.

That is to say, the depth of field becomes shallow when the aperture 121 is opened and becomes deep when the aperture is narrowed. Therefore, when the image of the fundus oculi is photographed with the opening area of the aperture 121 being "LARGE" (opening aperture), the depth of field becomes shallow and the focusing range becomes narrow.

Therefore, when focusing the fundus oculi Ef, the image becomes clear only within a small range, and defocused ahead and behind of the range, so that it is easy to focus a position of the fundus oculi Ef to be observed.

For example, it is possible to focus the position of the fundus oculi Ef to be observed when the position is just set to the focusing range from blurred (defocused) state.

This is especially effective when an automatic focusing is used because the required time is greatly shortened.

Moreover, because the aperture 121 is set to "LARGE" when observing the fundus oculi, the light volume of the light entering the examinee's eye via the aperture 121 is increased in relation to in a case in which the aperture 121 is closed. Accordingly the observation light volume is reduced, and the observation light is brighten up.

In this manner, it is possible that the focus operation is easily carried out when photographing, and a suitable condition with the brighten light is provided so that the examiner easily observes the fundus oculi of the eye E.

When observing the fundus oculi, for example, if the aperture is opened while the observation light volume remains high, it is possible that the fundus oculi become too bright to show any details. Therefore, if the opening area of the aperture 121 is set to "LARGE" when photographing the image of the fundus oculi, the observation light volume is automatically adjusted to be reduced as well as in a case where the light volume is manually adjusted.

Because the observation light volume is reduced, the examinee is less dazzled. Also, the lower observation light volume reduces the possibility of pupil constricting caused by eclipses and flares.

As described above, it is possible to minimize the discomfort felt by the examinee during the observation because the examinee is less dazzled and the pupil constricting is prevented so that the discomfort felt by the examinee is minimized even though the observing operations takes a much longer period than the photographing operations.

When photographing the image of the fundus oculi, the opening area (opening aperture) of the aperture which is used when observing is narrowed, the depth of field is increased and the range in which the image appears to be in focused state is expanded. This makes it easier to obtain a focused photographed image.

Also, when photographing the image of the fundus oculi, because the aperture 121 is narrowed to the small opening area, therefore the illumination light and the photographing light are further divided, therefore the possibility of flares is reduced.

In this manner, since this prevents blurring and flares, it is possible that more defined image of the fundus oculi of the eye E is photographed. In the first embodiment, the observation light volume is automatically adjusted in accordance with the photographing opening area (opening aperture) of the aperture 121 when observing the fundus oculi; and the photographing light volume is automatically adjusted in accordance with a reduced amount of the opening area (=opening aperture–small opening area aperture) of the aperture 121 when photographing the image of the fundus oculi.

Therefore, the complex operations such as the manual adjustments to the photographing light volume is eliminated so that operability and efficiency are increased.

In the first embodiment, when the small opening area aperture (SMALL) with the depth of field being deep is set prior to photographing by the operation of the SMALL button, the opening area of the opening aperture (LARGE) of the aperture 121 when observing is narrowed to the set small opening area aperture (SMALL) when photographing the image of the fundus oculi.

Therefore, when photographing the image of the fundus oculi, it is not necessarily to narrow the aperture 121. For example, if the aperture 121 remains to be set in a opened state and the photographed image is required to be obtained, it is possible to obtain it by not intentionally pressing the small button 34a.

In the first embodiment, regardless of the photographing mode selection or the photographing medium selection, if the aperture of the small opening area aperture (SMALL) is set by the operation of "SMALL" button prior to photographing, the opening aperture (LARGE) of the aperture 121 provided when photographing the fundus oculi is narrowed to the set small opening area aperture (SMALL).

For example, when the photographing mode is the color mode and a condition that the medium type is the CCD camera is added, in the case that the photographing mode and the medium are other than the color mode and the CCD camera, the aperture is not narrowed when photographing, even when the small opening area aperture (SMALL) is selected.

On the other hand, only the selection of the small opening area aperture (SMALL) is set as a required condition to narrow the aperture 121 used when photographing so that it is possible to ensure more defined photographing of the image of the fundus oculi of the eye E in accordance with the small opening area aperture (SMALL).

The effects of the opthalmologic photographing apparatus 1 of the first embodiment are described as follows.

(1) An opthalmologic photographing apparatus 1, which is used to observe and photograph a fundus oculi of an eye to be examined, includes an observation light source illuminating the eye to observe the fundus oculi of the eye, a photographing light source illuminating the eye to photograph an image of the fundus oculi of the eye; an aperture through which light illuminated from either the observation light source or the photographing light source and reflected on the fundus oculi of the eye is observed or photographed, and a control device which is configured to control an opening area of the aperture, wherein the control device sets the opening area of the aperture to an opened observing opening area (LARGE) when observing the fundus oculi, and set from the observing opening area to a narrowed photographing opening area when photographing the image of the fundus oculi. Therefore, it is easy to observe the fundus oculi Ef while minimizing the discomfort on the examinee and the more defined image of the fundus oculi Ef can be obtained when photographing.

(2) The control device automatically adjusts an observation light volume in accordance with the opening area of the aperture 121 when observing the fundus oculi, and automatically adjusts a photographing light volume in accordance with a reduced amount of the opening area of the aperture 121 when photographing the image of the fundus oculi. Therefore, it is possible for the complex operation such as manual adjustments of the photographing light volume to be eliminated, so that the operability and efficiency of the apparatus is increased.

(3) The opthalmologic photographing apparatus includes an aperture setting device having a SMALL button 34a and a LARGE button 34b. The aperture setting device is configured to set a target opening area of the aperture by selecting one target opening area from a plurality of target opening areas. If the small opening area aperture (SMALL) is selected by the SMALL button 34a prior to photographing, the opened aperture (LARGE) of the aperture 121 is required to be narrowed to the set small opening area aperture (SMALL). Accordingly the examiner's intention is reflected by pressing or not the SMALL button 34a, and it is possible that different examiner's intentions in case that a defined fundus image of the eye E is required, or that an image of the fundus image when the aperture is under the "LARGE" setting is required are satisfied.

(4) Regardless of any photographing setting, since under the condition that it is required only that the small opening area aperture (SMALL) is set by selecting the "SMALL" button 34a prior to photographing, the aperture 121 when observing the fundus oculi is narrowed from the "LARGE" (opening aperture) of the aperture to the set "SMALL" (small opening area aperture) when photographing. Therefore regardless of the setting for photographing, it is possible that more defined photographing of the eye E is ensured in accordance with the selecting operation of the "SMALL".

Second Embodiment

The second embodiment is related to a case in which the size of the aperture 121 is reduced when photographing the peripheral portion of the fundus oculi Ef, the fundus oculi being inclined. In this case, photographing with a large depth of field is advantageous.

Since the structure of the second embodiment is similar to the first embodiment described in accordance with FIGS. 1 to 6, drawings and explanations will be omitted.

The operations of the second embodiment will now be described.

Figure 8:
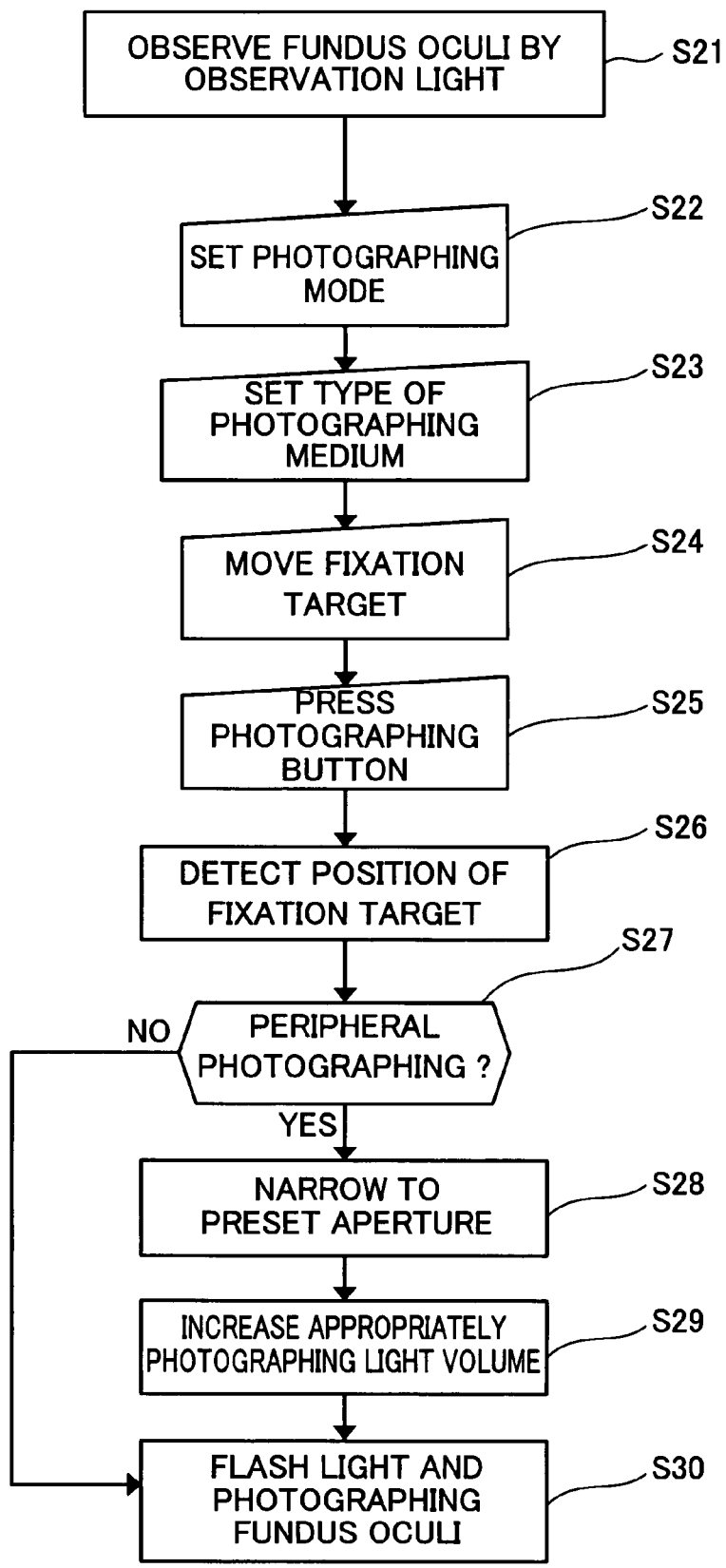
FIG. 8 is a flow chart illustrating an example of a process to observe and photograph a fundus oculi which is carried out by use of the opthalmologic photographing apparatus according to a second embodiment of the present invention.

FIG. 8 is a flow chart illustrating an example of the fundus oculi observation and photographing processes carried out by use of the opthalmologic photographing apparatus 1 according to the second embodiment of the present invention. The following sections describe the operations of the fundus oculi observation, the fundus oculi photographing and aperture switching between observing and photographing in accordance with FIG. 8.

[Fundus Oculi Observation]

In step S21, similarly to step S1 in FIG. 7, the aperture 121 is set to an opened state, and the light volume of the halogen lamp 101 is automatically reduced in accordance with the opening state of the aperture 121. The fundus oculi of the eye E is examined under a reduced observation light volume.

Therefore, the aperture 121 is set to "LARGE" (opening state) which is an initial state, and the light volume of the halogen lamp 101 is automatically reduced in accordance with the state of the aperture 121. Other operations are also the same as those in the first embodiment.

[Photographing Fundus Oculi of Eye]

In step S22, similarly to step S2 in FIG. 7, after the observing operation of the eye of the fundus oculi is finished, at first, one of the buttons 31a, 31b and 31c provided on the first control panel 30L is selectively pressed to set the photographing mode. When setting the photographing medium is not carried out, the color photographing mode corresponding to the button 31a is selected as the initial setting.

In step S23, similarly to step S3 in FIG. 7, one of the buttons 33a, 33b and 33c is selectively pressed to set the type of medium used in the first photographing device 9. When setting the type of the photographing medium is not carried out, the CCD camera corresponding to the button 33a is selected as the initial setting.

In step S24, the position of the external fixation target (external fixation lamp 7) is manually switched, or the position of the internal fixation target (on the LCD 109) is manually switched by manipulating the fixation target switch 35c. Therefore, the eye E is directed and the fixation target is shifted.

In step S25, after moving the fixation target in step S24, the button 4a is pressed as the fundus oculi photographing operation.

It should be noted that it is possible that the pressing operation of the photographing button 4a is started without setting operations in steps S22 and S23, and also without taking the fixation target movement in step S24.

In step S26, the position of the fixation target is detected by the fixation target position sensor 36 which detects at least one of positions, one is the position of the LCD 109 and the other is the position of the external fixation lamp 7.

In step S27, after detecting the position of the fixation target in step S26, it is determined whether the photographing region belongs to the peripheral portion of the fundus oculi based on the position detecting information of the fixation target. If yes, the process proceeds to step S28; and otherwise, the process proceeds to step S30.

Herein, when a position of the fixation target detected by fixation target position sensor 36 is a position deviates from a central position, in which the pupil of the eye is to be front, to a nose side or a ear side, it is determined that photographing is conducted as peripheral portion photographing.

Further, regardless of whether the color photographing mode selection (including the initial setting) and the CCD camera selection (including the initial setting) are established or not, when it is determined that the peripheral portion photographing is conducted, the process proceeds to step 28 in priority to these setting conditions.

In step S28, after the determination whether the photographing is peripheral portion photographing in step S27, a control command to narrow the opening area of the aperture 121 as the opening aperture (LARGE) to a preset target opening area with a depth of field being deep, and the control command is sent to solenoid 143.

Here, it is possible that the target opening area with the depth of field being deep, for example is the small opening area aperture "SMALL" described in the first embodiment, or in consideration of peripheral photographing the opening area aperture capable of obtaining larger depth of field than the small opening area aperture "SMALL". Furthermore, it is possible that the depth of field is increased and the opening area is set in a small area, as the fixation target deviates from a central position to a peripheral side, in accordance with a degree of deviation of the fixation target deviated from the central position to the nose side or ear side.

In step S29, after controlling to narrow the aperture 121 in step 28, the light volume of the halogen lamp 101 and the xenon lamp 103 is appropriately increased when photographing in accordance with the change of the opening area of the aperture 121, similarly to step 8.

In step S30, similarly to step S9, after the operation to increase the photographing light volume is conducted in step S29; or the determination that the photographing is not the peripheral portion photographing in step S27, the xenon lamp 103 (flash) is emitted to conduct fluorescence photographing of the image Ef' of the fundus oculi Ef of the eye E.

[Aperture Switching between Observation/Photographing]

When it is determined that the photographing is not peripheral portion photographing in step S27 when the process is shifted from the observation operation to the photographing operation, the actual process in the flow chart of FIG. 8 proceeds to step S21, step S22, step S23, step S24, step S25, step S26, step S27, and step S30, in this order.

Therefore, in step S30, the fluorescence photographing of the image Ef' of the fundus oculi Ef of the eye E is conducted while the aperture 121 remains "LARGE" (opening aperture).

On the other hand, when the process is shifted from the observation operation to the photographing operation, if it is determined that the photographing is peripheral portion photographing in step S 27, the actual process in the flow chart of FIG. 8 proceeds to step S21, step S22, step S23, step S24, step S25, step S26, step S27, step S28, step S29, and step S30, in this order.

Therefore, in step S28, the aperture 121 is narrowed from the "LARGE" (opening aperture) to a preset small opening aperture; in step S29, the aperture 121 is set in a condition that an appropriate photographing light volume when the aperture 121 is set to a small opening area aperture (SMALL) is obtained; and in step S30, the fluorescence photographing of the image Ef' of the fundus oculi Ef of the eye E is conducted.

Herein, a peripheral portion photographing of the fundus oculi Ef is different from a usual fundus oculi photographing in that:

The photographed portion is in a state where a spherical surface is inclined, therefore, the fundus oculi Ff which is object is inclined, large differences exist in the distance between each of the various sections to the fundus oculi Ef;

Since the focusing of a sprit type is not used for focusing because the illumination light beam and the photographing light beam are deviated from each other due to an eccentric of the cornea, the viewfinder (monitor) is used for visual determining;

Even though the amount of photographing light is increased by narrowing the aperture 121, the examinee is less dazzled in the peripheral portion photographing away from the macular region.

On the other hand, in the opthalmologic photographing apparatus of the second embodiment, when it is determined that the position of the fixation target detected by the fixation target position sensor 36 is a position when peripheral portion photographing, which deviates from the central position in which the pupil of the eye is to be front, to a nose side or a ear side, the opening area of the aperture is narrowed small when photographing the fundus image.

In other words, since the depth of field is being deep (small opening area aperture) when the peripheral portion photographing, while the depth (opening aperture) of field is small when observing before the photographing, the range in which the image appears to be in focus will also be increased. Therefore, the peripheral portion photographing in which the fundus oculi is inclined and the focusing of sprit type is not permitted allows a focused image to be obtained regardless of the peripheral photographing of the fundus oculi due to advantage of the depth of field being deep.

In the second embodiment, regardless of any setting relate to photographing, the opening area of the aperture which is set when observing is narrowed to a preset target opening area with a depth of field being deep only based on a condition that it is determined that the photographing is the peripheral portion photographing in which the position of the fixation target detected by the fixation target position sensor 36 is a position which deviates from the central position at which the pupil of the eye is to be front, to the position of the nose side or the ear side when photographing the fundus oculi.

For example, if the photographing mode is color mode and a condition that the medium type is CCD camera is added, the aperture is not narrowed, even if the peripheral portion photographing is conducted with other than the color mode and the CCD camera.

On the other hand, if only the peripheral photographing setting condition is set as a required condition to narrow the aperture 121, the more defined image of the fundus oculi of the eye can be ensured corresponding to the peripheral photographing operation in which the fixation target is shifted.

The effect of the opthalmologic photographing apparatus according to the second embodiment is described as follows.

In the opthalmologic photographing apparatus 1 of the second embodiment, it is possible to obtain the following effect add to the above-described effect (1) and (2) of the first embodiment.

(5) The opthalmologic photographing apparatus includes a fixation target position sensor 36 which is configured to detect a position of a fixation target at the eye. When it is determined that the photographing is the peripheral portion photographing in which a position of the fixation target detected by the fixation target position sensor 36 is a position which deviates from a central position at which a pupil of the eye is to be front, to a position of a nose side or a ear side, when photographing the image of the fundus oculi, the control device narrows the opening area of the aperture when observing. Therefore, it is possible that a more focused image is obtained, regardless of whether the fundus oculi is inclined and sprit focusing can not be used in the peripheral photographing.

(6) Regardless of any setting relate to photographing, the control device narrows the opening area of the aperture 121 when observing to a preset target opening area with a depth of field being deep only based on a condition that it is determined that the photographing is the peripheral photographing in which the position of the fixation target detected by the fixation target position sensor 36 is a position which deviates from the central position at which the pupil of the eye is to be front, to the position of the nose side or the ear side, when photographing the image of the fundus oculi. Therefore, it is possible that the size of the aperture is reduced regardless of the setting for photographing, and that a more defined photograph of the eye E is ensured.

Although the opthalmologic photographing apparatus of the present invention has been described in the first and second embodiments above, it is not intended that the present invention be limited to these embodiments. Various modifications and additions can be made without departing from the scope of the present invention, which is defined by the claims.

The first embodiment shows an example illustrating an opthalmologic photographing apparatus in which the aperture is narrowed when photographing only based on the condition that it is determined that the small opening area is selected; and the second embodiment shows an example illustrating an opthalmologic in which the aperture is narrowed when photographing only based on the condition that it is determined that the photographing is the peripheral portion photographing. However, for example, it is possible that the aperture is narrowed when photographing only based on the photographing operation in which the photographing button is pressed, and also based on the condition in which other conditions except the embodiments 1 and 2 is added. In summary, any opthalmologic photographing apparatus in which a larger aperture is used for observation and the aperture is narrowed when conducting fundus oculi photographing shall be regarded as within the scope of the present invention.

In the first and second embodiments, the aperture is set to a fixed and preset opening aperture (LARGE) when observing the fundus oculi. However, it is possible that the opening area of the fixed opening aperture is manually adjusted within a certain range.

The first and second embodiments illustrates the case in which the aperture is fixed to a preset small opening area aperture when photographing the fundus oculi or photographing the peripheral portion. However, it is also possible that the opening area of the fixed small opening area aperture is manually adjusted within a certain range. It is also possible that an optimal aperture area is set based on the capability of the camera. Moreover, it is possible that aperture information is recorded together with the image along with every photographing, and the opening area is manually adjusted to obtain an optimal image or it is also possible that the setting is automatically changed through machine learning.

The first and second embodiments shows examples illustrating the aperture which is controlled in multi-steps. However, it is possible that the opening area is controlled in a single step. It is possible that the opening area of the aperture is precisely adjusted in a case of the single step photographing aperture.

In the first and second embodiments, the photographing light volume is automatically compensated in accordance with the narrowed volume in the aperture. However, it is also possible that compensation of the photographing light volume is manually carried out.

The first and second embodiments shows examples illustrating the opthalmologic photographing apparatus which is configured to set and change the photographing mode and the photographing medium. However, for example it is also possible that the photographing mode is fixed to the color photographing with the CCD camera in the opthalmologic photographing apparatus. The first and second embodiments also describe an example opthalmologic photographing apparatus in which the focusing process is manually carried out. However, it is possible that an example of the opthalmologic photographing apparatus of autofocus-type is illustrated. In summary, any opthalmologic photographing apparatus having an observation light source for examining the fundus oculi of the eye and the photographing light source for photographing in which the light reflected on the fundus oculi is observed or photographed through an aperture, shall be applicable to the present invention.

Therefore, the control device used in the opthalmologic photographing apparatus of the present invention sets the opening area of the aperture to an observing opening area provide when observing the fundus oculi, and the opening area of the aperture is narrowed small when photographing.

That is, because the depth of field is reduced when opening the aperture and is increased when narrowing the aperture, the depth of field is reduced and the focused range is narrowed when observing the fundus. This makes it possible to focus an observing part of the fundus oculi. In addition, when observing the fundus oculi, the aperture is opened, so that the observation light is brightened even when the observation light volume is reduced. The ease of focusing and bright illumination helps to facilitate the observation of the fundus oculi.

When observing the fundus oculi, if a high observation light volume is maintained when increasing the aperture size, the fundus oculi will be too illuminated to show any details. Therefore, the observation light volume must be manually or automatically reduced when observing. Therefore, the observation light volume is reduced so that the examinee is less dazzled and the possibility of pupil constricting is reduced. This minimizes the discomfort felt by the examined.

When photographing, for example, if the aperture is opened while the high observation light volume is maintained, the fundus oculi is brightened over and it is difficult to observe a detailed part, regardless of whether manual or automatic operation, the observation light volume would be controlled lower. Since the observation light volume becomes lower, glare affecting the examinee will be reduced. Because the observation light volume becomes lower, the constricted pupil of the pupil is hard to occur. The glare reduction and the prevention of the constricted pupil makes it possible to minimize the discomfort to the examinee when observing.

When photographing the image of the fundus oculi, the aperture is narrowed smaller while observing, the depth of field is shifted from a shallow state to a deep state, and the focusing range is increased in relation to the narrow range. Therefore it is easy to obtain a focused photographing image. In addition, when photographing, the aperture is narrowed smaller, an illumination light beam and a photographing light beam are more separated, so that the possibility of flares is reduced. The fundus oculi of the eye is clearly photographed by preventing blurring and flares when photographing.

As a result, when observing the fundus oculi, the observation of the fundus oculi is facilitated while minimizes the discomfort on the examinee, and while clearly photographing the image of the fundus oculi.

What is claimed is:

1. An opthalmologic photographing apparatus which is used to observe and photograph a fundus oculi of an eye to be examined, comprising:
 an observation light source illuminating the eye to observe the fundus oculi of the eye;
 a photographing light source illuminating the eye to photograph an image of the fundus oculi of the eye;
 an aperture through which light illuminated from either the observation light source or the photographing light source and reflected on the fundus oculi of the eye is observed or photographed; and
 a control device which is configured to control an opening area of the aperture,
 wherein the control device sets the opening area of the aperture to an opened observing opening area when observing the fundus oculi, and to a narrowed photographing opening area when photographing the image of the fundus oculi.

2. The opthalmologic photographing apparatus according to claim 1, wherein the control device automatically adjusts a light volume of the observation light source in accordance with the observing opening area of the aperture, and automatically adjusts a light volume of the photographing light source in accordance with a narrowed amount of the opening area of the aperture from the observing opening area to the photographing opening area.

3. The opthalmologic photographing apparatus according to claim 2, further including an aperture setting device, which is configured to set a target opening area of the aperture by selecting one target opening area from a plurality of target opening areas,
 wherein when the opening area of the aperture is set to a target photographing opening area with a depth of field being deep to photograph the image of the fundus oculi prior to photographing, the control device narrows the opening area of the aperture to the target photographing opening area to observe the fundus oculi during photographing the image of the fundus oculi.

4. The opthalmologic photographing apparatus according to claim 3, wherein when photographing the image of the fundus oculi, the control device narrows down the observing opening area of the aperture to the set target photographing opening area, regardless of any setting relate to photographing, and only based on a condition that as the opening area of the photographing aperture a target photographing opening area with a depth of field being deep is set prior to photographing.

5. The opthalmologic photographing apparatus according to claim 2, further including a fixation target position detection device which is configured to detect a position of a fixation target on the eye,
 wherein when a position of the fixation target detected by the fixation target detection device is determined to be a peripheral photographing that deviates from a central position at which a pupil of the eye faces a front, to a position of a nose side or a side of each ear, when photographing the image of the fundus oculi, the control device narrows the observing opening area of the aperture.

6. The opthalmologic photographing apparatus according to claim 5, wherein regardless of any setting relate to photographing, only based on a condition that when the position of the fixation target detected by the fixation target detection device is determined to be the peripheral photographing that deviates from the central position at which the pupil of the eye faces the front, to the position of the nose side or the side of each ear, when photographing the image of the fundus oculi, the control device narrows the observing opening area of the aperture to a preset target opening area with a depth of field being deep.

7. The opthalmologic photographing apparatus according to claim 1, further including an aperture setting device, which is configured to set a target opening area of the aperture by selecting one target opening area from a plurality of target opening areas,
 wherein when the opening area of the aperture is set to a target photographing opening area with a depth of field being deep to photograph the image of the fundus oculi prior to photographing, the control device narrows the opening area of the aperture to the target photographing opening area to observe the fundus oculi during photographing the image of the fundus oculi.

8. The opthalmologic photographing apparatus according to claim 7, wherein when photographing the image of the fundus oculi, the control device narrows the observing opening area of the aperture to the set target photographing opening area, regardless of any setting relate to photographing, and only based on a condition that as the opening area of the aperture a target photographing opening area with a depth of field being deep is set prior to photographing.

9. The opthalmologic photographing apparatus according to claim 1, further including a fixation target position detection device which is configured to detect a position of a fixation target on the eye,
 wherein when a position of the fixation target detected by the fixation target detection device is determined to be a peripheral photographing that deviates from a central position at which a pupil of the eye faces a front, to a position of a nose side or a side of each ear, when photographing the image of the fundus oculi, the control device narrows the photographing opening area of the aperture.

10. The opthalmologic photographing apparatus according to claim 9, wherein regardless of any setting relate to photographing, only based on a condition that when the position of the fixation target detected by the fixation target detection device is determined to be the peripheral photographing that deviates from the central position at which the pupil of the eye faces the front, to the position of the nose side or the side of each ear, when photographing the image of the fundus oculi, the control device narrows the observing opening area of the aperture to a preset target opening area with a depth of field being deep.

* * * * *